US008506975B2

(12) United States Patent
Laba et al.

(10) Patent No.: US 8,506,975 B2
(45) **Date of Patent: *Aug. 13, 2013**

(54) COSMETIC COMPOSITIONS UTILIZING A SILICONE-FREE HYDROCARBON COMPLEX

(75) Inventors: Dennis Laba, Langhorne, PA (US); Priti Shah, Piscataway, NJ (US); Marie Yednak-Carpenter, Jackson, NJ (US)

(73) Assignee: Presperse Corporation, Somerset, NJ (US)

( * ) Notice: Subject to any disclaimer, the term of this patent is extended or adjusted under 35 U.S.C. 154(b) by 125 days.

This patent is subject to a terminal disclaimer.

(21) Appl. No.: 12/634,036

(22) Filed: Dec. 9, 2009

(65) Prior Publication Data

US 2010/0143426 A1 Jun. 10, 2010

Related U.S. Application Data

(60) Provisional application No. 61/121,317, filed on Dec. 10, 2008.

(51) Int. Cl.

| | |
|---|---|
| *A61K 8/02* | (2006.01) |
| *A61K 9/00* | (2006.01) |
| *A61K 8/00* | (2006.01) |
| *A61K 8/18* | (2006.01) |
| *A61Q 17/04* | (2006.01) |
| *A61Q 5/08* | (2006.01) |
| *A61Q 19/02* | (2006.01) |
| *A61Q 1/02* | (2006.01) |
| *A61Q 1/12* | (2006.01) |
| *A61Q 19/04* | (2006.01) |
| *A61Q 1/04* | (2006.01) |
| *A61Q 1/06* | (2006.01) |
| *A61Q 15/00* | (2006.01) |
| *A61Q 1/00* | (2006.01) |

(52) U.S. Cl.

USPC .............. 424/401; 424/400; 424/59; 424/62; 424/63; 424/64; 424/65; 424/69

(58) Field of Classification Search

None

See application file for complete search history.

(56) References Cited

U.S. PATENT DOCUMENTS

| | | | | |
|---|---|---|---|---|
| 3,439,088 | A * | 4/1969 | Edman | 424/63 |
| 5,824,323 | A * | 10/1998 | Fishman | 424/401 |
| 5,891,237 | A | 4/1999 | Kinniard | |
| 5,961,997 | A * | 10/1999 | Swinehart | 424/401 |
| 6,352,688 | B1 * | 3/2002 | Scavone et al. | 424/65 |
| 2004/0241200 | A1 | 12/2004 | Winn et al. | |
| 2004/0247552 | A1 * | 12/2004 | Blin et al. | 424/70.13 |
| 2006/0127341 | A1 | 6/2006 | Lion et al. | |
| 2007/0191497 | A1 * | 8/2007 | Dransfield et al. | 516/20 |
| 2007/0224140 | A1 * | 9/2007 | Quadir et al. | 424/63 |
| 2008/0044483 | A1 | 2/2008 | Kessell | |
| 2008/0107697 | A1 | 5/2008 | Blin et al. | |
| 2008/0112990 | A1 | 5/2008 | Russ et al. | |
| 2008/0193404 | A1 | 8/2008 | Lange et al. | |

OTHER PUBLICATIONS

Derwent abstract for Berber et al., WO 2004/052327, pub. Jun. 2004.*

International Search Report and Written Opinion for corresponding PCT Application No. PCT/US2009/67302, Feb. 3, 2010. (Form PCT/ISA/220/210/237).

International Preliminary Report on Patentability and Written Opinion for corresponding PCT application No. PCT/US2009/067302, Jun. 14, 2011. (PCT/IB/326/373/ISA/237).

* cited by examiner

*Primary Examiner* — Isis Ghali

(74) *Attorney, Agent, or Firm* — Timothy X. Gibson, Esq.; Gibson & Dernier LLP

(57) ABSTRACT

Silicone-free compositions including hydrocarbons of widely different structures and origins combined with coated particles are provided which have both aesthetic and volatility properties similar to cyclopentasiloxane dispersions. The compositions are useful as full or partial replacement products for dispersions of cyclopentasiloxane, or "volatile silicones." The compositions are useful in UV-attenuating formulations including skin care products, color cosmetics, pharmaceutical products and especially sun care products such as sunblocks, sunscreens, tanning lotions, and the like.

14 Claims, No Drawings

COSMETIC COMPOSITIONS UTILIZING A SILICONE-FREE HYDROCARBON COMPLEX

CROSS-REFERENCE TO RELATED APPLICATIONS

This application claims the benefit of U.S. Provisional Patent Application Ser. No. 61/121,317 filed Dec. 10, 2008, the entirety of which is incorporated herein by reference.

FIELD OF THE INVENTION

The present invention relates in general to silicone-free dispersions of materials, and particularly to cosmetic dispersions using silicone-free hydrocarbon complexes.

BACKGROUND OF THE INVENTION

Dispersions of titanium dioxide in various liquid carriers are used by cosmetic chemists for UV protection in sunscreen products and in daily wear cosmetics such as foundations and moisturizers. These systems typically use special chemicals to help fully disperse the titanium dioxide in the carrier, and to keep the dispersion viscosity as low as possible so higher levels of the powder can be incorporated. These special chemicals are called “dispersing agents” or “wetting agents” and typically include polyhydroxystearate, or Isopropyl titanium triisostearate. One disadvantage of adding these additional chemicals to the dispersion is that their presence could affect the eventual stability of the finished sunscreen formula by interfering with the delicately balanced emulsifier system, as they are usually surface-active compounds themselves. Since the majority of consumer sunscreen products are emulsion-based, and potential instability may take up to several months to present itself, this can cause time delays during the formulation screening process. Also, the addition of a wetting agent to a dispersion has typically been necessary to achieve both a high concentration of titanium dioxide and a low dispersion viscosity; the high concentration being advantageous due to minimized shipping costs of the raw material, and the low dispersion viscosity being advantageous due to the formulating flexibility it offers.

Sunscreen technology has been changing recently to keep up with consumer preferences. Ease of sunscreen application is becoming increasingly important to consumers, as is evidenced by the increased number of sunscreen spray-on products introduced to the market. In order to design these products to spray properly, a low formulation viscosity is preferable. In addition, consumers are becoming more aware of the safety of the ingredients used in their cosmetic products. In particular, the use of silicone and silicone-based products has drawn negative attention from the media. Silicone and its derivatives have been used as the primary carrier, wetting agent or coating agent in a number of commercially available sunscreen dispersions that formulators have come to depend on. However, silicone and its derivatives, though widely used in cosmetics for many years, are once again undergoing scrutiny for their safety as well as environmental impact. In view of this situation, silicone and its derivatives may fall out of favor with consumers, requiring formulators to find suitable substitutes if they are to continue providing dispersion-based sunscreen products. Thus there is a need for silicone-free, aesthetically pleasing carriers that can contain large amounts of particulate sunscreens without building inordinate amounts of viscosity, without wetting agents and coatings on the titanium dioxide that contain silicone derivates.

SUMMARY OF THE INVENTION

Embodiments of the current invention overcome the problems of the prior art by utilizing a complex of silicone-free hydrocarbons that provides the same aesthetics as the currently-used silicones. Surprisingly, it has been found that when choosing a coated particle such as titanium dioxide to be used in a silicone-free carrier fluids as disclosed herein, the particle coating itself plays a much more important role than traditionally thought. It has been found that by carefully selecting a coated particle for compatibility between the coating and the carrier fluid, it is possible to provide a dispersion composition, such as one appropriate for use in a sunscreen, that is not only totally silicone-free and dispersant- or wetting agent-free, but also provides for highly concentrated dispersions in extremely low-viscosity products.

OBJECTS OF THE INVENTION

It is an objective of this invention to provide to the cosmetic industry, as well as other industries that use dispersed ingredients, a suitable raw material that is totally silicone-free.

It is a further objective that the new materials can be dispersant-free, yet exhibit very low, fluid viscosity in spite of the fact that they contain high concentrations of the active dispersion.

In one embodiment a non-silicone-based composition which approximates the volatility and aesthetics of cyclomethicone is used as the main carrier fluid of a dispersion composition containing a particular titanium dioxide powder that is also silicone-free.

In accordance with a preferred embodiment the present invention contains a non-silicone-based composition as a carrier fluid which approximates the volatility and aesthetics of cyclomethicone having about 35% C12-C14 isoparaffin, about 55% C13-C16 isoparaffin, and about 10% C13-C15 alkane. It also contains titanium dioxide powder, base-coated with aluminum hydroxide, with an outer coating of isostearic acid.

Compositions of the present invention are useful in UV attenuating formulations including skin care products, color cosmetics, pharmaceutical products and especially sun care products such as sunblocks, sunscreens, tanning lotions, and the like. The compositions are easily formulated for sprayable application due to their low viscosity.

DETAILED DESCRIPTION OF THE INVENTION

In the following description, for purposes of explanation, specific numbers, materials and configurations are set forth in order to provide a thorough understanding of the invention. It will be apparent, however, to one having ordinary skill in the art that the invention may be practiced without these specific details. In some instances, well-known features may be omitted or simplified so as not to obscure the present invention. Furthermore, reference in the specification to “one embodiment” or “an embodiment” means that a particular feature, structure or characteristic described in connection with the embodiment is included in at least one embodiment of the invention. The appearances of the phrase “in one embodiment” in various places in the specification are not necessarily all referring to the same embodiment.

In one embodiment the present invention comprises dispersion compositions including coated solid particles, for example coated titanium dioxide particles, and a hydrocarbon carrier liquid, with no wetting agent. Surprisingly, dispersions according to the present invention may be highly concentrated, especially those including a specially-coated titanium dioxide grade, yet exhibit a fluid, pourable viscosity. The dispersions preferably include a carrier liquid comprising a combination of hydrocarbons that together exhibit aesthetic properties similar to the family of products known as cyclomethicones, or "volatile silicones."

Suitable particles for use in the dispersions of the present invention include but are not limited to coated metal oxide products such as titanium dioxide and zinc oxide, coated pigments, and coated mineral powders such as talc, sericite, mica and the like. When a metal oxide particle is used the desirable particle size is from 10 to 150 nm. When the selected particle includes an appropriate outer coating the particles may be employed in silicone-free dispersions without the use of wetting agents. Particularly useful particles are available commercially from Kemira as UV Titan M160 and M161. A titanium dioxide product that is particularly well-suited for use in the dispersions of the present invention is available from Tayca, and is sold as MT-150EX. MT-150EX is a commercial grade of micro-fine titanium dioxide for UV protection. The MT-150EX powder has a base crystal particle size of 15 nanometers, a base coating of aluminum hydroxide, and an outer coat of isostearic acid. It will be apparent to the skilled artisan that a composition may include more than one type of coated particle, such as a mixture of coated titanium dioxide and coated zinc oxide, etc.

Suitable outer coatings may include isostearic acid, stearic acid and dimethicone/methicone-based coatings. Without being confined to a single theory, it is believed the outer coating of the titanium dioxide particles of MT-150EX contributes to the surprisingly good compatibility of the particles with the carrier fluid. As evidenced by the embodiments described herein, when the particle outer coating and the carrier fluid are both carefully chosen, the compatibility can be high enough to obviate the need for a wetting agent.

Through the selective use of highly compatible coating materials, dispersions in mixed hydrocarbon carriers, such as SiClone™ SR-5, commercially available from Presperse LLC, can be prepared with high powder concentrations, while the viscosity is kept low.

In one embodiment the carrier is a non-silicone-based carrier composition which approximates the volatility and aesthetics of cyclomethicone, wherein the carrier includes at least two volatile hydrocarbon components and at least one nonvolatile hydrocarbon component. Examples of such compositions are disclosed in U.S. Published Patent Application No. US-2009-0123398-A1, the entirety of which is incorporated herein by reference.

In accordance with another embodiment the non-silicone-based carrier has a first volatile hydrocarbon component selected from a C12-C14 hydrocarbon and a second volatile hydrocarbon component selected from a C13-C16 hydrocarbon and a nonvolatile hydrocarbon component. The volatile hydrocarbon components may be one or more straight or branched chain hydrocarbons, one or more isoparaffins such as a C12 to C14 isoparaffin or isododecane. The nonvolatile hydrocarbon component may include a C13 to C21 hydrocarbon, and may be a mixture of isoalkanes and mixed structure hydrocarbons selected from linear, branched and cyclohydrocarbons. In one embodiment the nonvolatile hydrocarbon component is a C13 to C16 alkane or a C13 to C16 isoparaffin. In another embodiment, the nonvolatile hydrocarbon may be selected from a C13 to C21 straight or branched chain alkyl ester of straight or branched chain carboxylic acid having 13 to 21 carbon atoms, and mineral oil.

In accordance with a preferred embodiment the carrier is a non-silicone-based mixed hydrocarbon composition which approximates the volatility and aesthetics of cyclomethicone having about 35% C12-C14 isoparaffin, about 55% C13-C16 isoparaffin, and about 10% C13-C15 alkane.

Specific examples of suitable carriers are hydrocarbons such as Isododecane and Isohexadecane manufactured by INEOS and distributed by Presperse LLC as Permethyl (R) 99A and Permethyl 101A respectively, and the Gemseal line of alkanes available from Total Petrochemicals, also distributed by Presperse LLC. Similar Isoparaffins manufactured by Exxon are also suitable. The skilled artisan will recognize other combinations of hydrocarbons or emollients may also work. The preferred carrier liquid is SiClone™ SR-5 manufactured by and available from Presperse LLC. The SiClone™ SR-5 carrier liquid is composed of three different hydrocarbons (C12-14 Isoparaffin, C13-16 Isoparaffin and C13-15 Alkane).

Concentrations of up to 40% by weight of titanium dioxide can be readily achieved by one skilled in the art when combining a suitable particle having a suitable outer coating and suitable carrier in accordance with the present invention. The prior art has not been able to achieve low viscosity dispersions containing 40% titanium dioxide without the use of wetting agents. Commercially available sunscreen dispersions with low viscosities and high concentrations of titanium dioxide use wetting agents/dispersants to achieve that viscosity. Without those additives, products with high concentrations of titanium dioxide are not considered flowable, but are designated as "pastes," with significantly higher viscosities.

In a most preferred embodiment a dispersion composition includes MT-150EX and SiClone™ SR-5. The MT-150EX which is a coated special grade of titanium dioxide and the SiClone™ SR-5 hydrocarbon complex exhibit an unexpected level of compatibility, and as such, the titanium dioxide powder easily disperses into the carrier liquid using conventional mixing techniques without the help of any typically needed chemical wetting agents.

As will be apparent to those having skill in the art, other compatible ingredients may be added to the dispersion compositions of the present invention. Examples of such other compatible ingredients can include, but are not limited to, branched-chain, linear or aromatic hydrocarbons; esters; natural or synthetic oils and waxes as well as solids such as the mineral powders already mentioned or oil-dispersible active ingredients. These ingredients may be used to modify the properties of the dispersion compositions, such as the application properties; or the compositions of the present invention may be used as a carrier or a delivery form, reducing the number of ingredients the formulating chemist has to add individually. If these types of ingredients are used, they should be added after the coated particle is initially dispersed in the carrier fluid, to preserve the special compatibility between those two ingredients.

In one embodiment the present invention comprises essentially a fluid, titanium dioxide sunscreen dispersion which needs no wetting agent, yet exhibits a high degree of dispersion efficiency comprising approximately 60% by weight of a hydrocarbon-based carrier fluid, and approximately 40% by weight of a suitably coated titanium dioxide as the powdered active ingredient. In this embodiment utility may be found at least in (1) the potential for additional stability of sunscreen products formulated with it, due to the absence of any interfering wetting agents, and (2) the ease of sunscreen formulating in both the laboratory and the plant, since the composition contains a high level of active ingredient, yet exhibits a dispersion viscosity low enough to be easily pourable or pumpable.

A preferred embodiment of a dispersion composition in accordance with the present invention is described in Table 1.

TABLE 1

| Chemical Name | % w/w |
|---|---|
| Titanium dioxide, aluminum hydroxide, isostearic acid | 40 |
| C13-16 Isoparaffin, | 30 |
| C12-14 Isoparaffin | 22.5 |
| C13-15 Alkane | 5 |
| C18-21 Alkane | 2.5 |

EXAMPLES

The following examples show how dispersion compositions of the present invention can be used in formulated cosmetic products.

Example 1

An O/W Lotion with Sun Protection Properties

| Trade Name | INCI Name | Supplier | |
|---|---|---|---|
| PHASE A | | | |
| DEIONIZED WATER | Water | N/A | 36.45 |
| VEEGUM ULTRA | Magnesium Aluminum Silicate | RT Vanderbilt | 0.50 |
| KELTROL CG | Xanthan Gum | Kelco | 0.20 |
| GLYCERIN 99.7% USP | Glycerin | Jeen | 3.00 |
| BUTYLENE GLYCOL | Butylene glycol | Ruger | 1.00 |
| TRILON BD | Disodium EDTA | BASF | 0.05 |
| PHASE B | | | |
| PERMETHYL ® 104A | Polyisobutene | Presperse, LLC | 1.00 |
| JEECHEM SMS | Sorbitan Stearate | Jeen | 1.30 |
| PERMETHYL 101A | Isohexadecane | Presperse, LLC | 2.00 |
| MICROSLIP 519L | PTFE | Presperse, LLC | 1.50 |
| MICROPOLY 210 | Oxidized Polyethylene | Presperse, LLC | 2.50 |
| MICROPOLY 230L | Polyethylene | Presperse, LLC | 0.50 |
| LIPOMULSE 165 | Glyceryl Stearate (and) Peg-100 Stearate | Lipo Chemical | 4.00 |
| SiCLONE SR-5 | C13-16 Isoparaffin (and) C12-14 Isoparaffin (and) C13-15 Alkane | Presperse, LLC | 3.00 |
| SiCLONE TD-150 | Titanium Dioxide (and) C13-16 Isoparaffin (and) C12-14 Isoparaffin(and) C13-15 Alkane (and) Aluminum Hydroxide (and) Isostearic Acid (and) C18-21 Alkane | Presperse, LLC | 40.00 |
| PHASE C | | | |
| EUXYL PE 9010 | Phenoxyethanol (and) Ethylhexylglycerin | Schulke | 1.00 |
| PHASE D | | | |
| RED TOCOL ARCTIC CRANBERRY SEED OIL | *Oxycocccus Palustris* Seed Oil | Presperse, LLC | 1.00 |
| KALPARIANE | Caprylic/Capric Triglyceride (and) *Alaria Esculenta* Extract | Presperse, LLC | 1.00 |

Procedure (Example 1)

In a main vessel, add water and begin heating to 75-80° C. with a prop mixer. Add Disodium EDTA and mix well until dissolved. In a separate vessel, add Glycerin and Butylene Glycol. Disperse Veegum Ultra and Keltrol CG into the Glycerin and Butylene Glycol. Mix until a slurry forms. Add the slurry to the main vessel. Mix until uniform with prop mixer. In a separate vessel, add Phase B ingredients and heat to 75-80° C. with a prop mixer. Make sure phase is uniform and correct temperature before continuing. Add Phase B to Phase A with homogenization for 2-3 minutes with medium speed at 75-80° C. until uniform. Cool batch to 45° C. with prop mixing. Once at 45° C., add Phase C. Mix until uniform. Continue cooling to 40° C., add Phase D and mix until uniform. Add Phase E at 40° C. and mix well until uniform. Cool to 25° C.

Example 2

A Sprayable Sunscreen Milk for Use on the Face and Body

| Trade Name | INCI Name | Supplier | % W/W |
|---|---|---|---|
| PHASE A | | | |
| SiClone SR-5 | C13-C16 Isoparaffin (and) C12-C14 Isoparaffin (and) C13-C15 Alkane | Presperse, LLC | 33.80 |
| Propyl Paraben NF | Propylparaben | Jeen | 0.10 |
| PHASE B | | | |
| SiClone TD-150 | Titanium Dioxide (and) C13-16 Isoparaffin (and) C12-14 Isoparaffin (and) C13-25 Alkane (and) Aluminum Hydroxide (and) Isostearic Acid (and) C18-21 Alkane | Presperse, LLC | 40.00 |
| PHASE C | | | |
| Deionized Water | Water | N/A | 25.00 |
| Methyl Paraben NF | Methylparaben | Jeen | 0.10 |
| Sodium Chloride USP | Sodium Chloride | N/A | 1.00 |

(Procedure Example 2)

In a main vessel, combine Phase A ingredients with propeller mixing. Add Phase B to Phase A and mix until uniform. Combine Phase C with propeller mixing. Add Phase C to Phase AB and mix until uniform. Pour into appropriate containers.

Example 3

A Sunscreen Lotion Using Both Chemical and Physical Sunscreens

| Trade Name | INCI Name | Supplier | % W/W |
|---|---|---|---|
| PHASE A | | | |
| Deionized water | Water | N/A | 58.15 |
| Glycerin 99.7% USP | Gylcerin | Jeen International | 2.00 |
| Disodium EDTA | Disodium EDTA | N/A | 0.05 |
| PHASE B | | | |
| Butylene Glycol | Butylene Glycol | N/A | 0.50 |
| Keltrol | Xanthan Gum | Kelco | 0.30 |
| PHASE C | | | |
| PERMETHYL 246C | $C_{18-21}$ Alkane (and) Polyisobutene | PRESPERSE LLC | 5.00 |
| SiClone TD-150 | Titanium Dioxide (and) $C_{13-16}$ Isoparaffin (and) $C_{12-14}$ Isoparaffin (and) $C_{13-15}$ Alkane (and) Aluminum Hydroxide (and) Isostearic Acid (and) $C_{18-21}$ Alkane | PRESPERSE LLC | 15.00 |
| Lipomulse 165 | Glyceryl Stearate (and) PEG-100 Stearate | Lipo Chemical | 3.00 |
| Lipowax D | Cetearyl Alcohol (and) Ceteareth-20 | Lipo Chemical | 1.50 |
| Stearic Acid | Stearic Acid | N/A | 1.50 |
| Escalol 557 | ethylhexylmethoxycinnamate | ISP | 5.00 |
| PHASE D | | | |
| Micropoly 230L | Polyethylene | PRESPERSE LLC | 1.00 |
| Spheron L-1500 | Silica | PRESPERSE LLC | 3.00 |
| PHASE E | | | |
| Beautifruit | Hydrolyzed Mango Juice Extract (and) Hydrolyzed *Garcinia Mangostama* fruit Extract (and) Hydrolyzed *Anona Cherimola* Fruit Extract | PRESPERSE LLC | 3.00 |
| Euxyl PE-9010 | Phenoxyethanol (and) ethylhexylgylcerin | Schülke | 1.00 |

(Procedure Example 3)

In a main kettle, combine Phase A in the order listed with prop mixer (medium speed 25-30° C.). In a separate vessel, combine Phase B ingredients in the order listed. Add Phase B to Phase A with prop mixer and heat to 70-75° C. Combine Phase C ingredients in the order listed and heat to 70-75° C. Mix until uniform. Slowly add Phase C to Phase AB with medium to high prop mixing (70-75° C.). Add Phase D to batch continue mixing at medium to high speed for 5-10 minutes. Add Phase E in the order listed to batch (medium speed at 35-40° C.). Cool to room temperature.

In further embodiments, sunscreen agents other than titanium dioxide or zinc oxide may be added to the dispersion compositions of the present invention to boost the UV-A or UV-B protective levels of the finished dispersion, being complementary to the protection offered by the inorganic additives which make up the primary dispersed material of the composition. These agents, which may be organic in nature and often liquid, may include the list of approved sunscreen actives for use in various countries, especially such as the list of approved sunscreen actives found in the US FDA Final Sunscreen Monograph, May 21, 1999 (64 FR 27666). This list includes, in addition to titanium dioxide and zinc oxide, aminobenzoic acid (PABA), avobenzone, cinoxate, dioxybenzone, ensulizole, homosalate, meradimate, octinoxate, octisalate, octocrylene, oxybenzone, padimate O, sulisobenzone, and trolamine salicylate.

In another embodiment, a dispersant, or wetting agent, may be included in the dispersion composition to still further reduce the viscosity of the resulting dispersion. While one novel aspect of the present invention resides in the low viscosity dispersions achieved without the use of a wetting agent, it is clear that since the ultimate goal of a dispersion may sometimes be to provide as high a concentration of the dispersed material with as low a viscosity as possible, the additional use of a wetting agent in the dispersion composition may indeed help to achieve that goal. The use of a wetting agent may allow a more concentrated form of dispersion to be prepared. The effect of combining the inventive dispersions with a wetting agent, in some cases, may be preferred. If a manufacturer desires the final modified dispersion to be literally "silicone-free," then the wetting agent must be selected with that restriction in mind.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A silicone-free composition comprising:

a carrier fluid component consisting of about 35% by weight of a first hydrocarbon component selected from a C12-C14 isoparaffin, about 55% by weight of a second hydrocarbon component selected from a C13-C16 isoparaffin, and about 10% by weight of at least one further component selected from the group consisting of a $C_{13}$-$C_{15}$ alkane and a cosmetically acceptable oil, and at least one coated particle dispersed in the carrier fluid, the particle selected from a metal oxide, a mineral and a pigment, the silicone-free composition comprising a cosmetically acceptable carrier, wherein the silicone-free composition does not include a wetting agent.

2. The composition according to claim 1 wherein the at least one coated particle is selected from one or more of the group consisting of coated titanium dioxide, coated zinc oxide, a coated pigment, coated talc, coated sericite and coated mica.

3. The composition according to claim 1 wherein the particle is a metal oxide particle with a particle size from about 10 nm to about 150 nm.

4. The composition according to claim 1 wherein the at least one coated particle comprises titanium dioxide.

5. The composition according to claim 1 wherein the at least one coated particle comprises zinc oxide.

6. The composition according to claim 1 comprising a first coated particle comprising titanium dioxide and a second coated particle comprising zinc oxide.

7. The composition according to claim 1 wherein the coated particle comprises a coating selected from isostearic acid and stearic acid.

8. The composition according to claim 1 wherein the coated particle is titanium dioxide and the coating of the coated particle comprises a base coating of aluminum hydroxide and an outer coating of isostearic acid.

9. The composition according to claim 1 comprising 40% by weight of the at least one coated particle.

10. The composition of claim 1, wherein at least one of the first or second hydrocarbon components comprises isododecane.

11. A cosmetic or personal care formulation comprising the composition of claim 1 and a cosmetically acceptable carrier.

12. A formulation according to claim 11 wherein the formulation is one of a hair care formulation, skin care formulation, a make-up formulation, a color cosmetic formulation, a tanning formulation, a deodorant formulation or an antiperspirant formulation.

13. A sun screen formulation comprising the composition of claim 1 and a cosmetically acceptable carrier.

14. A pharmaceutical cream or lotion formulation comprising the composition of claim 1 and a pharmaceutically acceptable carrier.

* * * * *